United States Patent [19] [11] 4,453,014
Van der Weerdt [45] Jun. 5, 1984

[54] PERFUME COMPOSITIONS AND PERFUMED ARTICLES CONTAINING ONE OR MORE TETRAMETHYL-TRI-CYCLOUNDECYL-ALKYL KETONES AS PERFUME BASE

[75] Inventor: Antonius J. A. Van der Weerdt, Huizen, Netherlands

[73] Assignee: Naarden International N.V., Ca Naarden-Bussum, Netherlands

[21] Appl. No.: 417,206

[22] Filed: Sep. 13, 1982

[30] Foreign Application Priority Data

Sep. 16, 1981 [NL] Netherlands ........................ 8104273

[51] Int. Cl.[3] ........................................ C07C 49/115

[52] U.S. Cl. ................................ 568/373; 252/522 R; 568/349

[58] Field of Search ................................ 568/373, 349

[56] References Cited

U.S. PATENT DOCUMENTS 4,053,657 10/1977 Schreiber et al. .............. 252/522 X
4,142,997 3/1979 Maurer ................................ 568/373

FOREIGN PATENT DOCUMENTS 2351650 12/1977 France .
7411659 3/1974 Netherlands .
7313920 4/1974 Netherlands .

OTHER PUBLICATIONS von K. H. Schulte-Elte et al. Helvetica Chimica Acta–vol. 54, Fasc. 1 (1971) Nr. 41, pp. 370–397.
G. Sosnovsky, *Free Radical Reactions in Preparative Organic Chemistry*, MacMillan, New York (1964), pp. 125–145.
K. Suga et al., Aust. J. Chem. 20, 2033–36 (1967).
L. A. Kheifits et al. Zh. Org. khim. 5, 1590–93 (1969).

*Primary Examiner*—James H. Reamer
*Attorney, Agent, or Firm*—Brumbaugh, Graves, Donohue & Raymond

[57] ABSTRACT

Perfume compositions, perfumed materials and perfumed articles containing one or more isomers of substituted 1.4.4.8-tetramethyl-tricyclo[6.3.0.0$^{2.5}$]-undecanes as perfume base.

Use of one or more isomers of 9-alkanoyl-1.4.4.8-tetramethyl-tricyclo[6.3.0.0$^{2.5}$]undecanes having formula

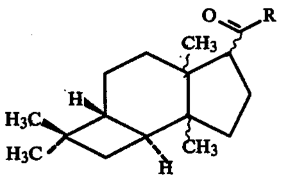
(1)

wherein R is methyl, ethyl or n-propyl as a perfume component in perfume compositions and in imparting fragrance to materials and articles for example soaps, cleaning preparations and cosmetic preparations.

4 Claims, 1 Drawing Figure

Figure 1:
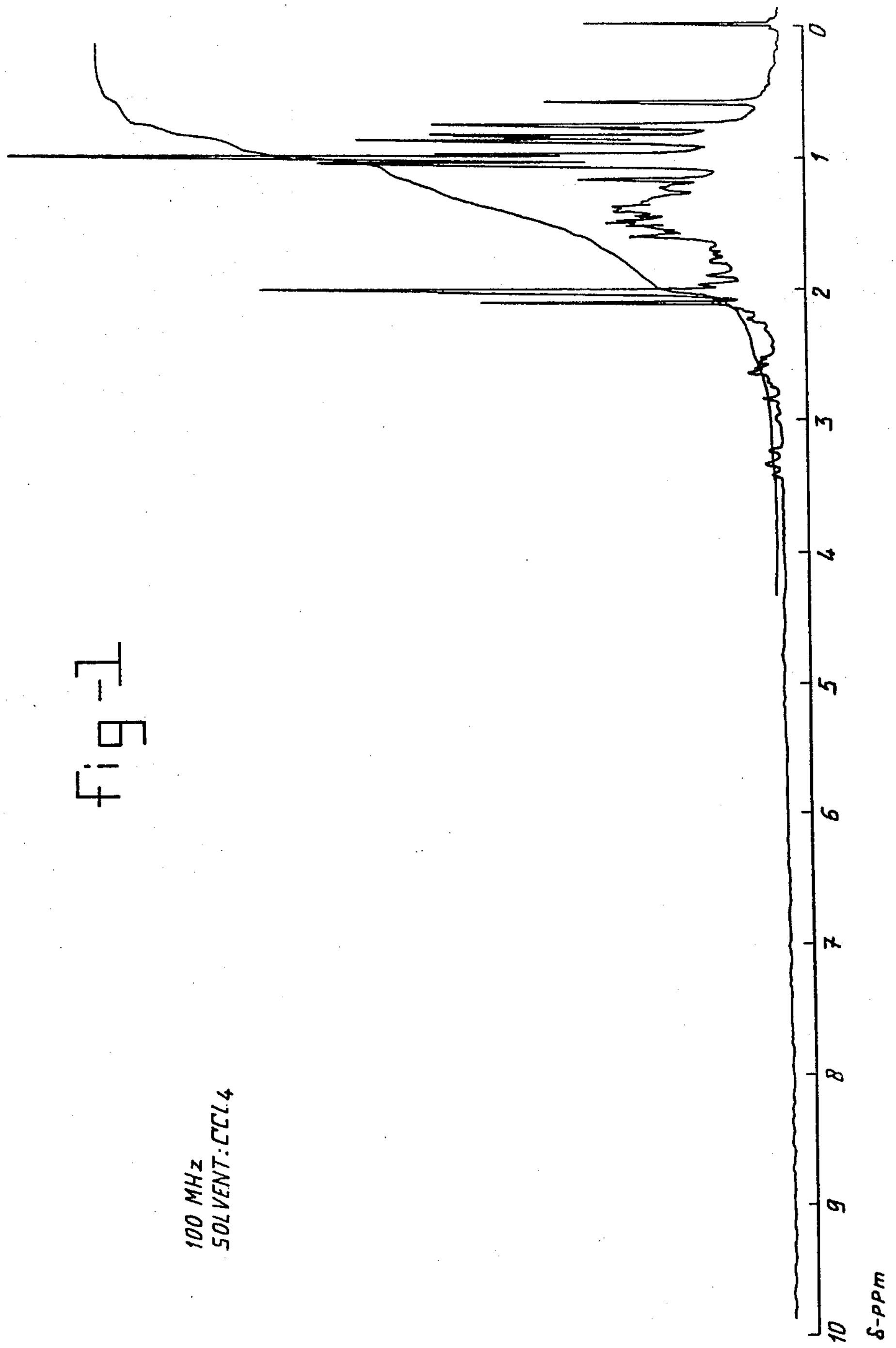

PERFUME COMPOSITIONS AND PERFUMED ARTICLES CONTAINING ONE OR MORE TETRAMETHYL-TRI-CYCLOUNDECYL-ALKYL KETONES AS PERFUME BASE

The invention relates to perfume compositions containing one or more tetramethyl-tricycloundecyl alkyl ketones as perfume base and to articles perfumed with these compounds. Further the invention relates to perfume compositions and perfumed articles containing the reaction product of the radical addition of acetaldehyde, propanal or n-butanal to caryophyllene as perfume base. Finally the invention relates to new tetramethyl tricyclo-undecyl alkyl ketones.

There is a continuing interest in the preparation and application of synthetic fragrances because these fragrances always can be prepared in the quantity desired and with uniform quality, contrary to the naturally occurring substances. Moreover many natural fragrances as well as synthetic fragrances developed in the past do not fulfill the present high requirements concerning chemical and olfactory stability. Therefore the perfume industry has to develop new synthetic fragrances which may fulfill these requirements.

It has been found that isomers of 9-alkanoyl-1.4.4.8-tetramethyl-tricyclo[6.3.0.$0^{2.5}$]undecanes having the following formula

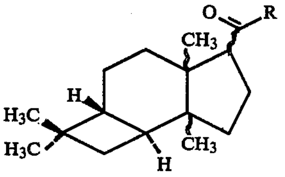
(1)

in which R is a methyl-, ethyl- or n-propyl group are valuable fragrances having pleasant woody and ambergris or spicy odor notes. In formula 1 the wavy lines symbolize the possibilities for the different stereochemical configurations.

Fragrances having a tricyclo[6.3.0.$0.^{2.5.}$]undecaneringsystem are unknown. K. H. Schulte-Elte and G. Ohloff, Helv. Chim. Acta 54, 370–397 (1971) describe 1.4.4.8-tetramethyl-tricyclo-[6.3.0.$0^{2.5}$]undec-10-ene

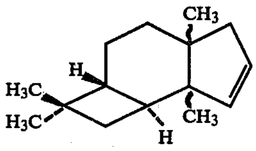
(2)

but do not report olfactory properties. Other compounds having such ringsystem are not known in the literature so that the compounds according to the invention are new.

The compounds according to the invention may be prepared by the reaction of acetaldehyde respectively propanal or n-butanal with caryophyllene under the influence of a radical-initiator. This reaction has been described for alkenes and aldehydes in G. Sosnovski, Free Radical Reactions in Preparative Organic Chemistry, MacMillan, New York (1964), pages 125–145 and more in particular for some alkenic terpenes by among others K. Suga and S. Watanabe, Aust. J. Chem. 20, 2033–2036 (1967) and L. A. Kheifits and G. I. Hina, Zh. Org. Khim. 5, 1636–1639 (1969) and in U.S. Pat. No. 4,053,657. The reaction can be carried out with suitable radical-initiators like di-tert.butyl peroxide, dibenzoyl peroxide and bisazoisobutyronitril. The reaction can also be initiated in a photochemical way by means of for instance benzophenone, acetophenone or a α-diketone like diacetyl. Such reaction for kamphene has been described in above mentioned U.S. patent specification.

The ketone represented by formula 1 has several stereo-isomers. The ring bond of the four-membered ring and the six-membered ring is as indicated in formula 1 and corresponds with the ring bond in caryophyllene.

Which other stereo-isomers are formed and in which mutual ratio depends on the type and the reagents of the specific reaction conditions. For instance the reaction product of the acetaldehyde addition under the influence of di-tert.butyl peroxide consists for 90% of a mixture of stereo-isomers represented by the following formulas

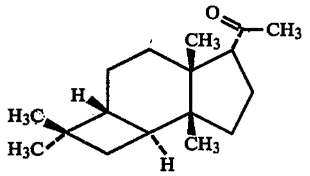
(1a)

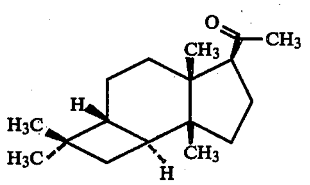
(1b)

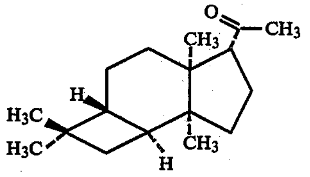
(1c)

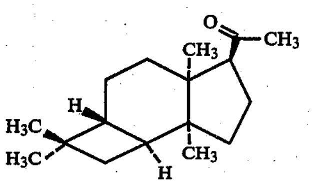
(1d)

In said mixture the amount 1a+1b is almost equal to the amount 1c+1d. The photochemical reaction with diacetyl, however, results in the same isomers but the ratio of the amounts of 1a+1b and 1c+1d is 2:1. Further 1a can be converted by isomerisation under the influence of a base into 1b; the same counts for 1c into 1d. An alkaline isomerisation of the total reaction mixture results therefore in a mixture substantially consisting of 1b+1d.

The different stereo-isomers which are obtained in the preparation of the compounds according to the invention can be separated by means of known technics for instance by means of gaschromatography on a capillary or packed column having a polar stationary phase like Carbowax 20M or Ucon at for instance 150°–200° C.

For the use as a fragrance it is not necessary to separate the isomers. Even for economical reasons a mixture of isomers is preferred. Therefore the invention also includes the use of a reaction product obtained by radical addition of acetaldehyde, propanal or n-butanal to caryophyllene as a fragrance.

Both the separate isomers and the mixtures of isomers can be used succesfully in perfume compositions or as such as odor imparting agent. Although the odors of the different isomers differ in nuances they all possess generally the already mentioned woody and the somewhat ambergris and spicy odor notes. Therefore these compounds may impart or strengthen such odor notes in perfume compositions or the articles to be perfumed.

The phrase "perfume composition" is used to mean a mixture of fragrances and optionally auxiliary substances that may be dissolved in an appropriate solvent or mixed with a powdery substrate used to impart a desired odor to the skin and/or various products. Examples of said products are: soaps, washing agents, dish washing and cleaning agents, air refreshers and room sprays, pommanders, candles, cosmetics such as creams, ointments, colognes, pre- and after shaving lotions, talcum powders, hair care agents, body deodorants and antiperspirants.

Fragrances and mixtures thereof which in combination with the compounds according to the invention can be used for the preparation of perfume compositions include natural products such as essential oils, absolutes, resinoids, resins, concretes etc., synthetic fragrances, such as hydrocarbons, alcohols, aldehydes, ketones, ethers, acids, esters, acetals, ketals, nitrils etc., both saturated and unsaturated compounds, aliphatic, carbocyclic and heterocyclic compounds.

Fragrances to be used in combination with the compounds according to the invention include geraniol, geranyl acetate, linalool, linalyl acetate, tetrahydrolinalool, citronellol, citronellyl acetate, myrcenol, myrcenyl acetate, dihydro myrcenol, dihydro myrcenyl acetate, tetrahydro myrcenol, terpineol, terpinyl acetate, nopol, nopyl acetate, β-phenyl ethanol, β-phenylethyl acetate, benzyl alcohol, benzyl acetate, benzyl salicylate, benzyl benzoate, amyl salicylate, styrallyl acetate, dimethylbenzyl carbinol, trichloro methylphenylcarbinyl acetate, p-ter.butyl cyclohexyl acetate, isononyl acetate, vetiveryl acetate, vetiverol, α-hexyl cinnamon aldehyde, 2-methyl-3-(p-tert.butylphenyl)-propanol, 2-methyl-3-(p-isopropyl phenyl)-propanol, 3-(p-tert.butylphenyl)-propanol, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydro pyran, 3-carboxymethyl-2-pentylcyclopentane, 2-n-heptyl cyclopentanone, 3-methyl-2-pentyl-2-cyclopentanone, n-decanal, n-dodecanal, 9-decenol-1, phenoxyethyl isobutyrate, phenyl acetaldehyde dimethylacetal, phenyl acetaldehyde diethylacetal, geranyl nitril, citronellyl nitril, cedryl acetate, 3-isocamphyl cyclohexanol, cedrylmethyl ether, isolongifolanon, aubepine nitrile, aubepine, heliotropine, coumarine, eugenol, vanilline, diphenyl oxide, hydroxy citronellal, ionones, methyl ionones, isomethyl ionones, irones, cis-3-hexenol and esters thereof, indan musk fragrances, tetraline musk fragrances, isochroman musk fragrances, macrocyclic ketones, macrolactone musk fragrances, ethylene brassylate, aromatic nitromusk fragrances.

Auxiliary agents and solvents that may be incorporated into perfume compositions according to the invention comprise, for example, ethanol, isopropanol, diethyleneglycol monoethylether, diethyl phthalate etc.

The amount of the esters that can be used in a perfume composition or in a perfumed product can be varied within broad limits and depends, for example, on the product wherein the perfume is used, the nature and the amount of the further components of the perfume compositions and the odor effect desired. Therefore, it is only possible to indicate very rough limits. However, these limits will give a person skilled in the art sufficient information concerning the odor strength and possibilities for the use of the compounds according to the invention. In most cases a quantity of only 0.01% in a perfume composition is sufficient to obtain a clearly observable odor effect.

In some cases, however, concentrations of 50% or more may be used in the compositions to impart specific odor effects.

In products perfumed with the aid of perfume compositions according to the invention the concentration is lower and depends on the quantity of the composition used in the product.

The following examples only illustrate the preparation and the use of the compounds according to the invention and do not restrict the invention thereto.

EXAMPLE I

Preparation of 9-acetyl-1.4.4.8-tetramethyl-tricyclo[6.3.0.$0^{2.5}$]undecane.

An ampoule of glass having a volume of 100 ml was filled with 20.4 g (0.1 mole) caryophyllene, 44 g (1 mole) acetaldehyde and 1.5 g (0.01 mole) di-tert.butyl peroxide. The air was removed by nitrogen. Then the ampoule was closed hermetically and heated during 3 hours at 125°–130° C. After that the ampoule was cooled off to room temperature and the contents was poured out in 100 ml 5%'s-soda solution. This mixture was extracted two times with toluene. The extract was dried above $MgSO_4$. Subsequently the toluene was removed by evaporation under reduced pressure. The residu was distilled and this distillate was fractionated, both under reduced pressure. Yield: 9.5 g (38%) reaction product; boiling point: 125°–140° C./0.7 kPa; $n_D^{20}=1.4950$. FIG. I shows an NMR-spectrum of this reaction product.

The so obtained reaction product had a pleasant woody odor with ambergris notes and consisted for about 90% of a mixture of the four isomers in the ratio (1a+1b):(1c+1d)=1:1. The mixture was gaschromatographically separated in two fractions which respectively contained isomer 1a and a mixture of the isomers 1b, 1c and 1d.

By mild heating of the reaction product with a methanolic solution of KOH a mixture was obtained substantially consisting of about equal quantities of the isomers 1b and 1d. Both GLC-fractions as well as the isomerized reaction product had a pleasant woody odor.

EXAMPLE II

Preparation of 9-propionyl-1.4.4.8-tetramethyltricyclo[6.3.0.$0^{2.5}$]undecane.

Above mentioned compound was prepared as described in example I from 80 g caryophyllene, 220 g propanal and 6 g di-tert.butyl peroxide in an ampoule of glass having a volume of 300 ml. Yield: 10 g reaction product; boiling point: 145°-150° C./0.3 kPa; $n_D^{23}=1.4930$.

The reaction product had a pleasant woody and somewhat spicy odor.

EXAMPLE III

A perfume composition is prepared according to the following receipt:

| | |
|---|---|
| Bergamot oil | 200 parts by weight |
| Citron oil Italian | 70 parts by weight |
| Hexyl salicylate | 50 parts by weight |
| γ-Methyljonon | 50 parts by weight |
| 6-Acetyl-1-isopropyl-2.3.3.5-tetra-methyl-indan | 40 parts by weight |
| Isolongifolanon | 40 parts by weight |
| Lavender absolute | 30 parts by weight |
| 3-Isocamphyl cyclohexanol | 30 parts by weight |
| Benzoe-resinoide Siam | 20 parts by weight |
| Patchouly oil | 20 parts by weight |
| Oak-moss absolute | 20 parts by weight |
| Lime oil West-Indian | 20 parts by weight |
| Galbanum resinoide | 20 parts by weight |
| Nerolidol | 20 parts by weight |
| Styrallyl acetate | 15 parts by weight |
| Methyl-dihydrojasmonate | 15 parts by weight |
| Oil of cloves | 10 parts by weight |
| Mixture of isomers obtained according to Example I | 80 parts by weight |
| | 750 parts by weight |

EXAMPLE IV

An aftershave lotion perfumed with a composition according to Example III was prepared according to the following receipt:

| | | |
|---|---|---|
| A | 1-Menthol | 0.3 parts by weight |
| | 2.2'.4.4'-tetrahydroxy-benzophenone | 0.5 parts by weight |
| | Propylene glycol | 30.0 parts by weight |
| | Ethanol | 535.0 parts by weight |
| B | Aluminum-chlorohydrate-allantoinate | 0.2 parts by weight |
| | Lactic acid | 2.0 parts by weight |
| | Water (distilled) | 400.2 parts by weight |
| C | Perfume (vide above) | 20.0 parts by weight |
| | Cremophor RH40+ | 10.0 parts by weight |
| | | 1000 parts by weight |

+trade mark of BASF for a reaction product of hydrogenated ricinus oil and epoxyethane.

The components mentioned under A, B and C were mixed separately to the mixtures A, B and C. Then mixture B was added to mixture A under good stirring. After that mixture C was added and the complete product was stirred homogeneously. So, a somewhat astringent and pleasantly smelling after-shave lotion was obtained.

EXAMPLE V

A perfume composition suitable for a modern detergent was prepared according to the following receipt:

| | |
|---|---|
| 2-Phenyl ethanol | 100 parts by weight |
| α-Pentyl cinnamic aldehyde | 100 parts by weight |
| 4-Acetoxy-3-pentyl-tetrahydropyran | 100 parts by weight |
| Benzyl salicylate | 80 parts by weight |
| Amyl salicylate | 80 parts by weight |
| Citronellol | 80 parts by weight |
| Dihydro myrcenol | 80 parts by weight |
| 6-Acetyl-1-isopropyl-2.3.3.5-tetramethyl-indan | 80 parts by weight |
| Benzyl acetate | 50 parts by weight |
| Nopyl acetate | 40 parts by weight |
| Musk ketone | 30 parts by weight |
| in alkaline way isomerised mixture of isomers obtained according to Example I | 80 parts by weight |
| | 900 parts by weight |

I claim:

1. Isomers of 9-alkanoyl-1.4.4.8-tetramethyl-tricyclo[6.3.0.0$^{2.5}$]undecanes having formula 1,

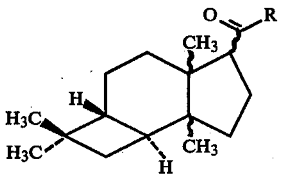

(1)

wherein R is methyl, ethyl or n-propyl.

2. Isomers of 9-alkanoyl-1.4.4.8-tetramethyltricyclo[6.3.0.0$^{2.5}$]undecane having formula 1,

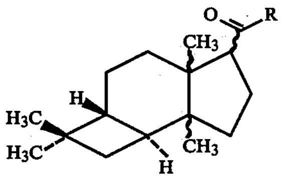

(1)

wherein R is methyl.

3. Reaction product obtained by radical-addition of respectively acetaldehyde, propanal and n-butanal to caryophyllene.

4. Reaction product according to claim 3 obtained by radical-addition of acetaldehyde to caryophyllene.

* * * * *